US007785566B2

(12) United States Patent
Cuthbertson et al.

(10) Patent No.: US 7,785,566 B2
(45) Date of Patent: Aug. 31, 2010

(54) PHARMACEUTICAL COMPOUNDS

(75) Inventors: Alan Cuthbertson, Oslo (NO); Bard Indrevoll, Oslo (NO); Morten Eriksen, Oslo (NO)

(73) Assignee: GE Healthcare, Inc., Oslo (NO)

( * ) Notice: Subject to any disclaimer, the term of this patent is extended or adjusted under 35 U.S.C. 154(b) by 1152 days.

(21) Appl. No.: 10/559,886

(22) PCT Filed: Nov. 5, 2004

(86) PCT No.: PCT/NO2004/000335

§ 371 (c)(1),
(2), (4) Date: Dec. 7, 2005

(87) PCT Pub. No.: WO2005/044313

PCT Pub. Date: May 19, 2005

(65) Prior Publication Data

US 2007/0134155 A1 Jun. 14, 2007

(30) Foreign Application Priority Data

Nov. 6, 2003 (NO) ............................ 20034952
Jul. 19, 2004 (GB) ............................ 0416062.8

(51) Int. Cl.
*A61K 51/00* (2006.01)
*A61M 36/14* (2006.01)
(52) U.S. Cl. .................. 424/1.69; 424/1.11; 424/1.65; 424/1.81; 424/1.85; 424/1.89; 424/9.1; 514/2; 514/5; 534/10; 534/14
(58) Field of Classification Search ............... 424/1.11, 424/1.65, 1.69, 9.1, 9.3, 9.4, 9.5, 9.6, 9.7, 424/9.8; 534/7, 10–16; 530/300, 316, 317, 530/328, 329, 330, 333, 338
See application file for complete search history.

(56) References Cited

U.S. PATENT DOCUMENTS 5,824,696 A * 10/1998 Griswold et al. ............. 514/382
7,521,419 B2 * 4/2009 Cuthbertson et al. .......... 514/10

FOREIGN PATENT DOCUMENTS

| DE | 19536783 A1 | 3/1997 |
|---|---|---|
| WO | 97/10852 | 3/1997 |
| WO | 98/18496 | 5/1998 |
| WO | 98/18498 | 5/1998 |
| WO | 02/064734 | 8/2002 |
| WO | 03/006070 | 1/2003 |
| WO | 03/006491 | 1/2003 |
| WO | 03/051859 | 6/2003 |

OTHER PUBLICATIONS

Katugampola Sidath D, et.al. "Changes in phenotypically transformed intimal smooth muscle layer of human atherosclerotic coronary arteries" Journal of Cardiovascular Pharmacology, vol. 36, No. 5, supplement 1, 2000, pp. S395-S396.
Sato Takaya, et.al., "Quantitative receptor autoradiographic analysis for angiotensin II receptors in bovine retinal microvessels: Quantitation with radioluminography" Cellular and Molecular Neurobiology, vol. 13, No. 3, 1993, pp. 233-245.
Healy, D.P., et.al., "Localization of central angiotensin II receptors with Iodine-125 Sar-1 Ile-8-Angiotensin II Periventricular Sites of the Anterior Third Ventricle" Neuroendocrinology, vol. 44, No. 1, 1986, pp. 15-21.
Shigematsu K, et.al., "Autoradiographic evidence of angiotensin II binding sites in the human adrenal gland" Biomedical Research 1988 Japan, vol. 9, No. 1, 1988, pp. 27-31.
Speth R.C. et.al. "Angiotensin II receptor localization in the canine CNS" Brain Research 1985 Netherlands, vol. 326, No. 1, 1985, pp. 137-143.
Bagby Susan P, et.al. "Ang II AT(1) and AT(2) receptors in developing kidney of normal microswine" American Journal of Physiology. Renal Physiology. Oct. 2002, vol. 283, No. 4, Oct. 2002, pp. F755-F764.
Heppeler A. et.al., "Receptor targeting for tumor localization and therapy with radiopeptides" Current Medicinal Chemistry, Bentham Science publishers BV, BE, vol. 7, No. 9, 2000, pp. 971-994.
Henze M, et.al. "PET imaging of somatostatin receptors using" Journal of Nuclear Medicine, New York, NY vol. 42, No. 7 pp. 1053-1056.
Int'l Search Report and Written Opinion PCT/NO2004/000335 dated Mar. 2006.

* cited by examiner

*Primary Examiner*—D L Jones
(74) *Attorney, Agent, or Firm*—Craig Bohlken

(57) ABSTRACT

The invention comprises pharmaceuticals of formula (I) $Z-(L)_n-V$, wherein V denotes a peptide, L denotes an optional linker, Z denotes a group that optionally can carry an imaging moiety M, n denotes 0 or 1. The pharmaceuticals are active as therapeutic agents for the treatment of heart failure, cardiac arrhythmias and diseases were fibrosis is prominent such as COPD, liver fibrosis and atherosclerosis and are also useful as diagnostic agents for the diagnosis of heart failure and diseases were fibrosis is prominent such as COPD, liver fibrosis and atherosclerosis.

6 Claims, 1 Drawing Sheet

PHARMACEUTICAL COMPOUNDS

This application is a filing under 35 U.S.C. 371 of international application No. PCT/NO2004/000335, filed Nov. 5, 2004, which claims priority to application number 20034952 filed Nov. 6, 2003 in Norway and application number 0416062.8 filed Jul. 19, 2004 in Great Britain the entire disclosure of which is hereby incorporated by reference.

FIELD OF INVENTION

The present invention provides novel pharmaceuticals useful in the treatment of heart failure, cardiac arrhythmia and other diseases where fibrosis is prominent and diagnosis of diseases and conditions where a fibrotic process is prominent. The invention further provides novel pharmaceutical compositions and precursors for the preparation of diagnostic agents. Further the invention provides novel pharmaceuticals useful in monitoring therapeutic treatment and methods for monitoring of treatment. Still further objectives of the invention are evident from the claims.

The novel pharmaceuticals comprise a targeting moiety that binds to a receptor that may or may not be up-regulated and/or over-expressed in the diseased area. The targeting moiety comprises a group which for imaging agents carry a diagnostically imageable moiety, an optional linker group and a peptide moiety.

The novel pharmaceutical compounds have high affinity for the Angiotensin Receptors, in particularly for the Angiotensin II (Ang II) type 1 ($AT_1$) receptor.

BACKGROUND OF INVENTION

Angiotensin II (Ang II)—the octapeptide (Asp-Arg-Val-Tyr-Ile-His-Pro-Phe)—is a pleiotropic vasoactive peptide that binds to two distinct receptors: the Ang II type 1 ($AT_1$) and type 2 ($AT_2$) receptors. Activation of the renin-angiotensin aidostrone system (RAAS) results in vascular hypertrophy, vasoconstriction, salt and water retention, and hypertension. These effects are mediated predominantly by $AT_1$ receptors. Paradoxically, other Ang II-mediated effects, including cell death, vasodilation, and natriuresis, are mediated by $AT_2$ receptor activation. The understanding of Ang II signaling mechanisms remains incomplete. $AT_1$ receptor activation triggers a variety of intracellular systems, including tyrosine kinase-induced protein phosphorylation, production of arachidonic acid metabolites, alteration of reactive oxidant species activities, and fluxes in intracellular $Ca^{2+}$ concentrations. $AT_2$ receptor activation leads to stimulation of bradykinin, nitric oxide production, and prostaglandin metabolism, which are, in large part, opposite to the effects of the $AT_1$ receptor. (See: Berry C, Touyz R, Dominiczak A F, Webb R C, Johns D G.: Am J Physiol Heart Circ Physiol. 2001 December; 281(6):H2337-65. Angiotensin receptors: signaling, vascular pathophysiology, and interactions with ceramide).

Ang II is the active component of the renin-angiotensin-aldosterone system (RAAS). It plays an important physiological role in the regulation of blood pressure, plasma volume, sympathetic nervous activity, and thirst responses. Ang II also has a pathophysiological role in cardiac hypertrophy, myocardial infarction, hypertension, chronic obstructive pulmonary disease, liver fibrosis and atherosclerosis. It is produced systemically via the classical RAAS and locally via tissue RAAS. In the classical RAAS, circulating renal-derived renin cleaves hepatic-derived angiotensinogen to form the decapeptide angiotensin I (Ang I), which is converted by angiotensin-converting enzyme (ACE) in the lungs to the active Ang II. Ang I can also be processed into the heptapeptide Ang-(1-7) by tissue endopeptidases.

The RAAS system is illustrated schematically in FIG. 1 hereto which is based on FIG. 1 in the article by Foote et al. in Ann. Pharmacother. 27: 1495-1503 (1993).

In addition to the RAAS playing an important role in the normal cardiovascular homeostasis, over activity of the RAAS has been implicated in the development of various cardiovascular diseases, such as hypertension, congestive heart failure, coronary ischemia and renal insufficiency. After myocardial infarction (MI), RAAS becomes activated. Specifically the $AT_1$ receptor seems to play a prominent role in post-MI remodelling, since $AT_1$ receptor expression is increased after MI and in left ventricular dysfunction. Therefore drugs that interfere with RAAS, such as ACE inhibitors and $AT_1$ receptor antagonists, have been shown to be of great therapeutic benefit in the treatment of such cardiovascular disorders.

For heart, kidneys, lungs and liver alike, fibrosis represents a common pathway to their failure. Understanding pathophysiologic mechanisms involved in organ fibrosis are therefore of considerable interest, particularly given the potential for protective pharmacological strategies. Tissue repair involves inflammatory cells, including members of the monocyte/macrophage lineage, integral to initiating the repair process; and myofibroblasts, phenotypically transformed interstitial fibroblasts, responsible for collagen turnover and fibrous tissue formation. Each of these cellular events in the microenvironment of repair are associated with molecular events that lead to the de novo generation of angiotensin II (Ang II). In an autocrine/paracrine manner, this peptide regulates expression of TGF-beta 1 via angiotensin ($AT_1$) receptor-ligand binding. It is this cytokine that contributes to phenotypic conversion of fibroblasts to myofibroblasts (myoFb) and regulates myofibroblast turnover of collagen. Angiotensin-converting enzyme (ACE) inhibition or $AT_1$ receptor antagonism each prevent many of these molecular and cellular responses that eventuate in fibrosis and therefore have been found to be protective interventions. (See: Weber K T. Fibrosis, a common pathway to organ failure: angiotensin II and tissue repair. Semin Nephrol. 1997 September; 17(5): 467-91 and references therein).

Ang II may regulate tissue fibrosis via the activation of mesenchymal cells. For example, Ang II stimulates the proliferation of cardiac fibroblasts in vitro via activation of $AT_1$. The presence of $AT_1$ receptors has also been demonstrated on cardiac fibroblasts in vitro. Most of the profibrotic effects of Ang II appear to be mediated via this receptor; however, increased $AT_2$ expression on cardiac fibroblasts has been detected in hypertrophied human heart, and the balance between the expression of these two subtypes may be critical in determining the response to Ang II.

(See: Am. J. Respir. Crit. Care Med., Volume 161, Number 6, June 2000, 1999-2004Angiotensin II is Mitogenic for Human Lung Fibroblasts via Activation of the Type 1 Receptor RICHARD P. MARSHALL, ROBIN J. MCANULTY, and GEOFFREY J. LAURENT and references therein).

The Ang II receptors can be distinguished according to inhibition by specific antagonists. $AT_1$ receptors are selectively antagonized by biphenylimidazoles, such as Losartan, whereas tetrahydroimidazopyridines specifically inhibit $AT_2$ receptors. The $AT_2$ receptor may also be selectively activated by CGP-42112A. This is a hexapeptide analog of Ang II, which may also inhibit the $AT_2$ receptor, depending on concentration). Two other angiotensin receptors have been described: $AT_3$ and $AT_4$ subtypes.

In rodents, the $AT_1$ receptor has two functionally distinct subtypes, $AT_{1A}$ and $AT_{1B}$, with >95% amino acid sequence homology.

The second major angiotensin receptor isoform is the $AT_2$ receptor. It has low amino acid sequence homology (~34%) with $AT_{1A}$ or $AT_{1B}$ receptors. Although the exact signaling pathways and the functional roles of $AT_2$ receptors are unclear, these receptors may antagonize, under physiological conditions, $AT_1$-mediated actions inhibiting cell growth and by inducing apoptosis and vasodilation. The exact role of $AT_2$ receptors in cardiovascular disease remains to be defined.

Other receptors for Ang II besides $AT_1$ and $AT_2$ are known and are generally referred to as $AT_{atypical}$ (see Kang et al., Am. Heart J. 127: 1388-1401 (1994)).

The suppression of Ang II's effects has been used therapeutically, for example in the management of hypertension and heart failure. This has been achieved in a number of ways: by the use of renin inhibitors which block the conversion of angiotensinogen to angiotensin I (the precursor to Ang II); by the use of angiotensin converting enzyme (ACE) Inhibitors that block the conversion of angiotensin I to Ang II (and also block bioconversion of bradykinin and prostaglandins); by the use of anti-Ang II-antibodies; and by the use of Ang II-receptor antagonists.

Beta blockers are most commonly used in treatment of arrhythmias. Anti-arrhythmic drugs have had limited overall success and calcium channel blockers can sometimes induce arrhythmias. No single agent shows superiority, with the possible exception of amiodarone. Short-term anti-arrhythmic benefit has been found to be offset by, depending on the specific drug, neutral or negative effects on mortality (Sanguinetti M C and Bennett, P B: Anti-arrhythmic drug target choices and screening. Circulation 2003, 93(6): 491-9257-263). Clearly better anti-arrhythmic drugs are needed.

A publication in Lancet (Lindholm, L H et al. Effect of Losartan on sudden cardiac death in people with diabetes: data from the LIFE study. The Lancet, 2003, 362: 619-620) revealed that $AT_1$ receptor antagonists in addition of being generally favourable to patients with CHF, also reduce the incidence of sudden cardiac death. There exist a few studies showing that $AT_1$ antagonists have an anti-arrhythmia effect on arrhythmias induced by myocardial infarct or in reperfusion after ligation of LAD (Harada K et al. Angiotensin II Type 1a Receptor is involved in the occurrence of reperfusion arrhythmias. Circulation. 1998, 97:315-317. Ozer M K et al. Effects of Captopril and Losartan on myocardial ischemia-reperfusion induced arrhythmias and necrosis in rats. Pharmacological research, 2002, 45 (4), 257-263 Lynch J J et al. EXP3174, the AII antagonist human metabolite of Losartan, but not Losartan nor the Angiotensin-converting enzyme inhibitor captopril, prevents the development of lethal ischemic arrhythmias in a canine model of recent myocardial infarction. JACC, 1999, 34 876-884).

DESCRIPTION OF RELATED ART

WO 98/18496 (Nycomed Imaging AS) discloses contrast agents comprising a vector-linker-reporter construct where the vector comprises angiotensin or a peptidic angiotensin derivative.

U.S. Pat. No. 4,411,881 (New England Nuclear Corporation) reads on stabilization of radio-labelled compounds. Examples of radio-labelled compounds include e.g. Angiotensin II (5-L-isoleucine) [tyrosyl-$^{125}$I]-(monoiodinated).

Ang II may be turned into potent antagonist or partial antagonists by changes in their amino acid composition. For instance substituting phenylalanine in position 8 with isoleucine and aspartic acid in position 1 with sarcosine; changes the peptide into a potent antagonist.

The specificity towards the $AT_1$ receptor may be increased by cyclisation or bridging of the amino acids in position 4 and 6. Similarly introducing sarcosine in position 1 and glycine in position 8 makes the peptide into a $AT_1$ selective antagonist (See R C Speth. Sarcosine11, glycine8 angiotensin II is an $AT_1$ angiotensin II receptor subtype selective anatagonist). Regulatory peptides 115 (2003) 203-209)

As mentioned above, the natural ligand to the $AT_1$ receptor is the octapeptide AngII, Asp-Arg-Val-Tyr-Ile-His-Pro-Phe, which binds to the $AT_1$ receptor in the nano-mole range.

When modifying a naturally binding ligand to a receptor by the binding of a moiety, in particularly with moieties that are relatively large and relatively bulky, the affinity of the peptide vector is frequently compromised.

We have surprisingly found that the octapeptide Ang II, Asp-Arg-Val-Tyr-Ile-His-Pro-Phe and derivatives thereof, when substituted in specific positions of the peptide not only retain its binding capability but surprisingly increases its affinity for the Angiotensin II receptors, in particular to the $AT_1$ receptor.

SUMMARY OF THE INVENTION

A first objective with the present invention is to provide pharmaceuticals useful in the treatment of heart failure, cardiac arrhythmias and other diseases were fibrosis is prominent such as in COPD, liver fibrosis, and atherosclerosis comprising a targeting moiety that demonstrate a higher binding affinity to the $AT_1$ receptor than the native octapeptide Ang II. The pharmaceutical should demonstrate antagonistic activity.

A second objective with the present invention is to provide pharmaceuticals useful in the diagnosis of heart failure and other diseases were fibrosis is prominent such as in COPD, liver fibrosis, and atherosclerosis comprising a targeting moiety incorporating an imageable moiety. The imageable moiety can be any imageable moiety which when administered to a subject can generate an image of at least a part of said subject to which said contrast agent has distributed, e.g. by radio imaging, SPECT, PET, MRI, X-ray, optical imaging (OI), ultrasound (US), electrical impedance or magnetometric imaging modalities. The targeting moiety incorporating the imageable modality should demonstrate a higher binding affinity to the $AT_1$ receptor than the Ang II and should preferably act as an antagonist although a weak agonistic activity may also be acceptable.

The new pharmaceuticals can hence be used sequentially or concurrently as a therapeutic agent when carrying a suitable imageable moiety for diagnostic imaging.

Further objectives comprise providing methods of treatment of hypertension, fibrosis, COPD and related diseases and methods of imaging of heart failure and fibrosis and also methods of monitoring of progression of treatment for such diseases and disorders as well as for related vascular diseases and disorders. The invention further provides novel pharmaceutical compositions and precursors for the preparation of diagnostic agents. Kits of diagnostic agents, in particular kits for the preparation of radiopharmaceutical diagnostic agents are also provided.

The pharmaceuticals of the invention comprise a peptide V, optionally a linker L and a moiety Z and can be visualised by the formula (I)

$$Z\text{-}(L)_n\text{-}V \qquad (I)$$

wherein
V denotes a peptide with a binding sequence —$X^1$—$X^2$-Val-Tyr-Ile-His-Pro-$X^3$,
L denotes an optional linker,
Z denotes a group that optionally can carry an imaging moiety M,
n is 0 or 1,
$X^1$ denotes an amino acid,
$X^2$ denotes Arg or N-alkylated Arg, or a mimetic of Arg,
$X^3$ denotes an amino acid containing a hydrophobic side-chain, and wherein the residues Val and Ile at position 3 and 5 respectively may optionally be replaced with amino acids capable of forming a bridge,
Z forms a bond with the amino acid $X^1$ optionally through the linker L, and M where present denotes an imageable moiety capable of detection either directly or indirectly in an diagnostic imaging procedure.

DETAILED DESCRIPTION OF THE INVENTION

Figure 1:
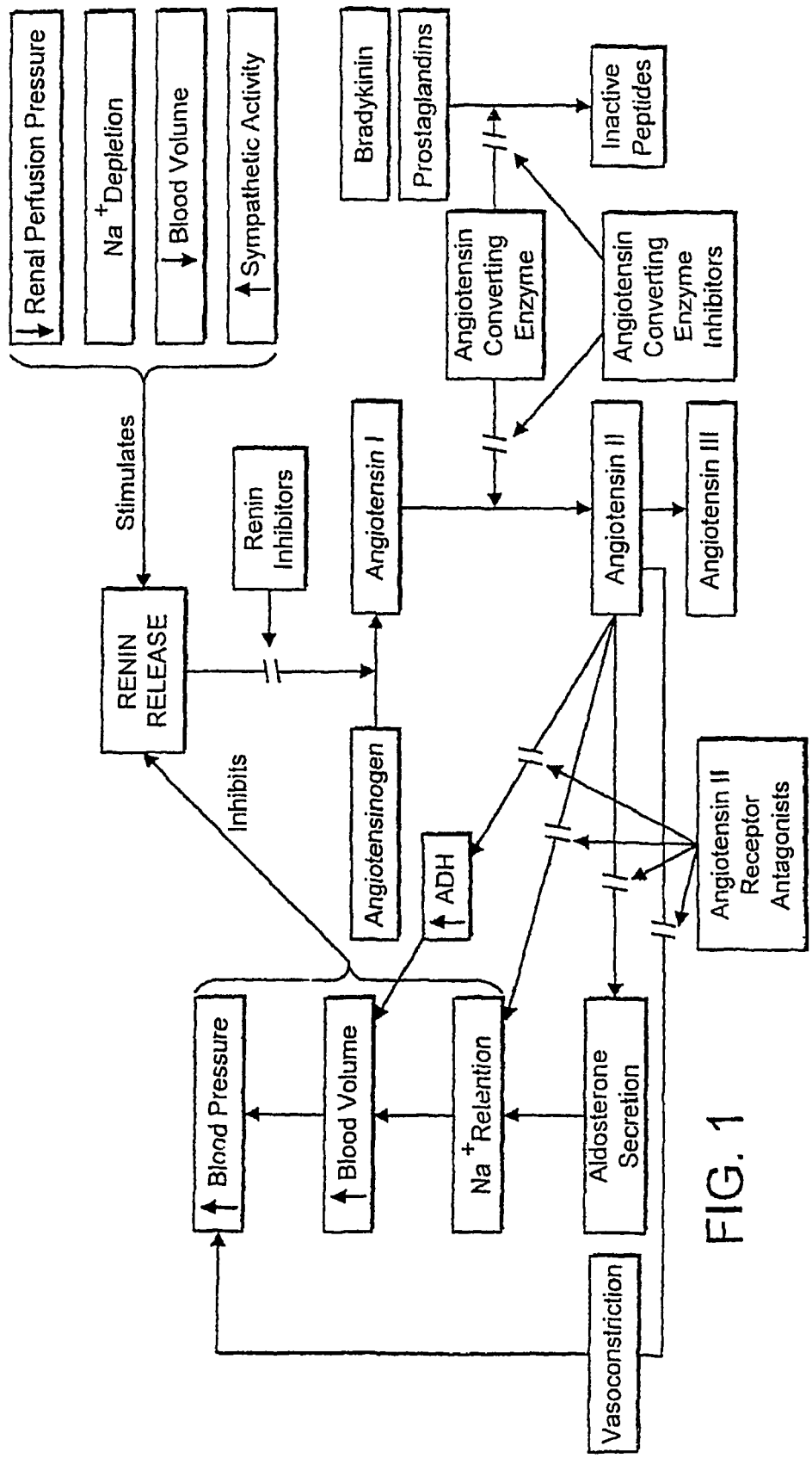
FIG. 1 is an illustration of the Renin Angiotensin Aldostrone System (RAAS).

The invention is described in the patent claims. Specific features of the invention are outlined in the following detailed description and the Examples.

In the targeting moiety of the formula (I) above V denotes the peptide sequence —$X^1$—$X^2$-Val-Tyr-Ile-His-Pro-$X^3$.

In the peptide V of formula (I) the amino acids are L-amino acids as in the native Ang II where not defined otherwise.

The three letter abbreviations used for the amino acids have the following meaning:
Arg—Arginine
Asp—Aspartic acid
Cys—Cysteine
Hcy—Homocysteine
Gly—Glycine
Sar—Sarcosine
Val—Valine
Tyr—Tyrosine
Ile—Isoleucine
His—Histidine
Pro—Proline
Phe—Phenylalanine
Abu—2-Amino-butyric acid
Nva—2-Amino-pentanoic acid
Nle—2-Amino-hexanoic acid
Phg—2-Amino-2-phenyl acetic acid
Hph—2-Amino-4-phenyl butanoic acid
Bip—2-Amino-3-biphenyl propionic acid
Nal—2-Amino-3-naphtyl propionic acid
Cha—2-Amino-3-cyclohexyl propionic acid The amino acids of V preferably are independently selected such that
$X^1$ denotes —$NY_1$—$(CH_2)_m$—CO— where m is an integer from 1 to 10 and $Y_1$ is H or an alkyl or aryl containing substituent, most preferred Gly
$X^2$ denotes Arg or N-Methyl-Arg or the Arg mimetics Phe[4-guanidino] and Gly-4-piperidyl[N-amidino],
$X^3$ denotes Phe, D-Phe, Ile, Abu, Nva, Nle, Phg; Hph, Bip, Nal or Cha, most preferred D-Phe, Bip, Ile or Hph.

Preferred are pharmaceuticals where $X^1$ denotes Gly, $X^2$ denotes Arg or N-Methyl-Arg and $X^3$ denotes D-Phe, Bip, Ile or Hph.

Still further preferred are pharmaceuticals where $X^1$ denotes Gly, $X^2$ denotes Arg and $X^3$ denotes Ile.

If the amino acids at position 3 and 5 are selected to form a bridging unit the bridge preferably containing a —$CH_2$—$CH_2$—, —S—$CH_2$—, —S—$CH_2$—S—, lactam or —S—S— unit. More preferred the covalent bond is a disulfide bond formed by oxidation of 2 cysteine or homocysteine pairings.

Examples of suitable linkers L are described in WO 98/18496 and in WO 01/77145 (pages 23 to 27) the content of which are hereby incorporated by reference. L may preferably represent a polyalkylene glycol unit such as polyethylene glycol (PEG) and polypropylene glycol (PPG), a carbohydrate, dextran or 1 to 10 amino acids. The linker may also serve as a biomodifier as described e.g. in WO 03/006491.

The linker L may also be derived from alkylamines or arylamines preferably compounds of the formula NH—(CH2)m- optionally combined with —CO—(CH2)m-CO— where m denotes a positive integer from 1 to 10.

The linker may also comprise one or more units of PEG as defined in formula IV hereinafter wherein n is an integer from 1 to 10.

Most preferred are linkers defined by formula (V) and (VI):

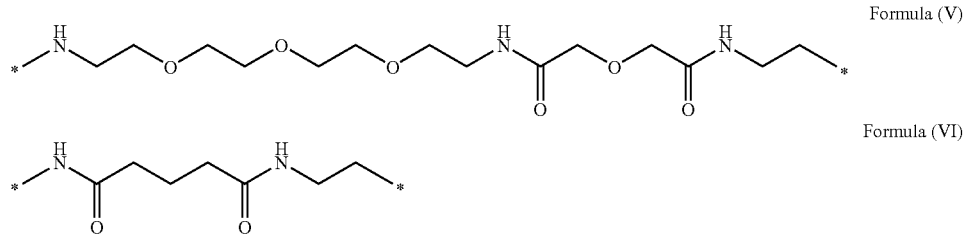

Formula (V)

Formula (VI)

The moiety Z comprises a non-peptidic moiety having a molecular weight of more than 50 D (Dalton), more preferably between 100 and 1000 D and still more preferably between 300 to 700 D. The moiety Z can be any pharmaceutically acceptable chemical entity provided that the resulting targeting moiety of formula (I) demonstrates a higher binding affinity to the $AT_1$ receptor than the native ligand Ang II. More specifically Z denotes an organic group having a suitable functional group such that Z can be reacted either with the linker L or directly with the peptide V to form a stable covalent bond.

Z can denote a straight or branched hydrocarbyl group optionally containing one or more double or triple bonds and optionally substituted by halogen, oxygen, sulphur of phosphorous atoms or optionally including heteroatoms such as oxygen, nitrogen or sulphur. More specifically the hydrocarbyl group can denote a substituted or unsubstituted alkyl, alkenyl, alkynyl groups having a molecular weight of at least 50 D.

Z can also denote one or more linked carbocyclic residues comprising monocyclic, bicyclic or tricyclic ring systems which can be saturated, partially unsaturated or aromatic and which can be substituted or unsubstituted and having a molecular weight of at least 50 D. Examples of such ring systems are aryl, aralkyl, cyclohexyl, adamantyl and naphthyl.

Z can further denote one or more linked heterocyclic compounds such as 5, 6, 7, 8, 9 or 10-membered ring systems which can be monocyclic, bicyclic or tricyclic and can contain one or more N, O, S and P as heteroatoms. Such ring systems can also be linked to hydrocarbyl and carbocyclic groups and defined above or fused to carbocyclic groups. Examples of such groups acridinyl, benzofuranyl, indolyl, pyridyl, piperidinyl, morphoridinyl and thienyl.

Z may also denote a polyalkylene glycol such as polyethylene glycol (PEG) and polypropylene glycol (PPG), a carbohydrate such as mono or polysaccharides all having a molecular weight in excess of 50 D. Polyalkylene glycols can additionally act as biomodifiers.

Specifically Z denotes a chelating agent such as acyclic or cyclic polyaminocarboxylates (e.g. DTPA, DTPA-BMA, DOTA and DO3A) as described e.g. in U.S. Pat. No. 4,647,447 (Schering AG) and WO 86/02841 (Nycomed Salutar, Inc.) which is hereby incorporated by reference. Further chelating agents comprises aminethiols such as diaminedithiols, amineoximes and hydrazines and related agents as described in WO 01/77145 (see Table I therein) which is hereby incorporated by reference. The chelating agent cPN216 of formula (VIII) is particularly preferred.

For pharmaceuticals useful in treatment Z can be any entity as described above.

For pharmaceuticals useful in diagnosis and particularly in in vivo diagnosis is the moiety Z must be able to carry the imageable moiety or moieties denoted M. By carrying is meant any form of association between the moiety Z and M such as a chemical bond, e.g. covalent bond or electrovalent or ionic bonds or by absorption or any other type of association.

Z can be any imageable moiety. Where M is a metal entity then $Y_1$ represents a chelating agent. The nature of Z and/or $Y_1M$ will depend of the imaging modality utilised in the diagnosis. Z and/or $Y_1M$ must be capable of detection either directly or indirectly in an in vivo diagnostic imaging procedure. eg. moieties which emit or may be caused to emit detectable radiation (eg. by radioactive decay, fluorescence excitation, spin resonance excitation, etc.), moieties which affect local electromagnetic fields (eg. paramagnetic, superparamagnetic, ferrimagnetic or ferromagnetic species), moieties which absorb or scatter radiation energy (eg. chromophores, particles (including gas or liquid containing vesicles), heavy elements and compounds thereof, etc.), and moieties which generate a detectable substance (eg. gas microbubble generators).

In a preferred embodiment one moiety Z is covalently bound directly to $X^1$ forming an N-alkyl glycine unit.

Chelating agents of formula (VII) and (VIII) hereinafter are also particularly preferred.

A wide range of suitable imageable moieties are known from e.g. WO 98/18496, the content of which is incorporated by reference.

Imaging modalities and imageable moieties Z and M are described in more detail hereinafter:

In a first embodiment, the compound of formula (I) comprises a moiety $Y_1$ carrying one or more imageable moieties M useful in the Radio and SPECT imaging modality. Preferably M is a gamma emitter with low or no alpha- and beta-emission and with a half-life of more than one hour. Preferred groups M are the radionuclides $^{67}Ga$, $^{111}In$, $^{231}I$, $^{125}I$, $^{131}I$, $^{81m}Kr$, $^{99}Mo$, $^{99m}Tc$, $^{201}Tl$ and $^{133}Xe$. Most preferred is $^{99m}Tc$.

M can further be represented by the following isotopes or isotope pairs for use both in imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

When M denotes a metallic radionuclide then $Y_1$ denotes a chelating agent suitable for forming a stable chelate with M. Such chelating agents are well known from the state of art and typical examples of such chelating agents are described in Table I of WO 01/77145.

Particularly preferred are chelating agents of formula (VII):

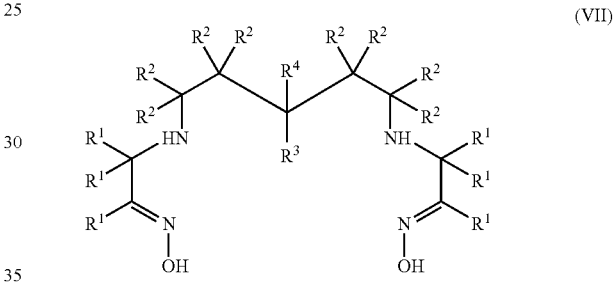

(VII)

wherein:
each $R^1$, $R^2$, $R^3$ and $R^4$ is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More particularly preferred are chelating agents of formula (VII) where $R^1$, $R^2$ and $R^3$ are hydrogen or methyl groups and $R^4$ is an alkylamine group, most specifically a compound of formula (VIII), herein denoted cPN126.

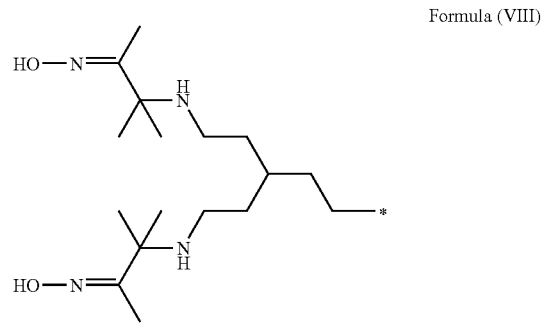

Formula (VIII)

Most preferred for $Y_1$ is when the chelate is cPN216 then the imaging moiety M is $^{99m}Tc$.

Synthesis of chelating agents of formula (VII) and (VIII) are described in WO 03/006070

Other preferred chelating agents are of formula (XI)

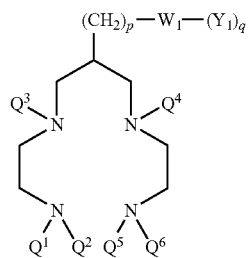
(XI)

wherein $Q_1$-$Q_6$ are independently Q groups, where Q is H, alkyl, aryl or an amine protecting group.
$W_1$ is —NR—, —$CO_2$—, —CO—, —NR(C=S)—, —NR(C=O)—, —CONR— or a Q group;
each Y is independently a D- or L-amino acid, —$CH_2$—, —$CH_2OCH_2$— or —$OCH_2CH_2O$— or an X group;
p is an integer of value 1 to 8;
q is an integer of value 0 to 30;
R is H, $C_{1-4}$ alkyl, $C_{2-4}$ alkoxyalkyl, $C_{1-4}$ hydroxyalkyl, or $C_{1-4}$ fluoroalkyl;
Q is

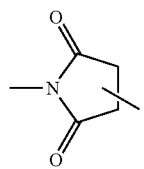

A is a counterion;
Synthesis of tetraamin chelting agents of formula (XI) can be found in GB patent application number GB 0416062.8.

Non-metal radionuclides such as $^{123}I$, $^{125}I$ and $^{131}I$ may be covalently linked to the moiety L when present or alternatively to $X_1$ by a substitution or addition reaction well known from the state of art.

In a second embodiment, the compound of formula (I) comprises a moiety Z useful in the PET imaging modality. Z then denotes a radioemitter with positron-emitting properties. Preferred groups Z are the radionuclides $^{11}C$, $^{18}F$, $^{88}Ga$, $^{13}N$, $^{15}O$ and $^{82}Rb$. $^{18}F$ is specifically preferred. The metallic radioemitters $^{82}Rb$ and $^{68}Ga$ chelated with a chelating agent $Y_1$ are also preferred.

Thiol coupling chemistry, $^{18}F$-synthons and labelled peptides prepared using the thiol coupling chemistry are described in WO 03/080544, the content of which is incorporated herein by reference.

Description of peptides labelled by use of thiol coupling chemistry can be found in GB patent application no. 0317815.9, the content of which is incorporated herein by reference.

When M denotes a metallic radionuclide then $Y_1$ denotes a chelating agent suitable for forming a stable chelate with M. Such chelating agents are well known from the state of art and typical examples of such chelating agents are described in Table I of WO 01/77145 and to the previous part on Radio and SPECT imaging.

In another preferred embodiment $Y_1$ is the DOTA chelating agent and M is $^{68}Ga$ which can be readily introduced in to the chelate using microwave chemistry.

Non-metal radionuclides such as $^{18}F$ may be covalently linked to the moiety L when present or alternatively to $X_1$ by a substitution or addition reaction well known from the state of art and also described eg. in WO03/080544 which is hereby incorporated by reference.

In a third embodiment, the compound of formula (I) comprises a moiety $Y_1$ carrying one or more imageable moieties M useful in the MR imaging modality. M here denotes a paramagnetic metal such those mentioned in U.S. Pat. No. 4,647,447, $Gd^{3+}$, $Dy^{3+}$, $Fe^{3+}$ and $Mn^{2+}$ are particularly preferred and $Y_1$ denotes a chelating agent, in particular a chelating agent such as acyclic or cyclic polyaminocarboxylates (e.g. DTPA, DTPA-BMA, DOTA and DO3A) as described e.g. in U.S. Pat. No. 4,647,447 and WO 86/02841. M may also denote metal oxides such as superparamagnetic, ferrimagnetic or ferromagnetic species which are absorbed by Z, e.g. such that Z function as a coating to the metal oxide. Metal oxides for use as MR contrast agents are described e.g. in U.S. Pat. No. 6,230,777 which is hereby incorporated by reference.

In a fourth embodiment the compound of formula (I) comprises a moiety $Y_1$ carrying one or more imageable moieties M useful in the X-ray imaging modality. M here denotes a heavy metal such as W, Au and Bi preferably in the form of oxides which may be absorbed to Z. Z can also be represented by iodinated aryl derivatives particularly well known as X-ray contrast agents, e.g. Iopamiron™ and Omnipaque™. These agents can be linked via their amide or amine functions to the peptide V of formula (I).

In a further embodiment the compound of formula (I) comprises Z in the form of gas filled microvesicles. Such ultrasound imaging agents can be utilised in the imaging of receptors e.g. when they are functionalised for binding to a peptide as described in the state of art e.g. in WO98/18500.

In a sixth embodiment of the present invention the moiety Z of formula (I) may be any moiety capable of detection either directly or indirectly in an optical imaging procedure. The detectable moiety can be a light scatterer (e.g. a coloured or uncoloured particle), a light absorber or a light emitter. More preferably Z is represented by a dye such as a chromophore or a fluorescent compound. The moiety Z can be any dye that interacts with light in the electromagnetic spectrum with wavelengths from the ultraviolet light to the near-infrared. In a preferred version Z has fluorescent properties.

Preferred organic dye moieties include groups having an extensive delocalized electron system, eg. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Further descriptions of moieties suitable in optical imaging procedures are found in Norwegian patent application no. 200303115 the content of which is hereby incorporated by reference.

The pharmaceutical of formula (I) may be further modified by the attachment of one or more biomodifier groups such as polyalkylene glycol unit e.g. polyethylene glycol (PEG) and polypropylene glycol (PPG). Examples of biomodifier groups are described in WO 03/006491 the content of which is hereby incorporated by reference. The biomodifier groups can be linked to any position in the compound of formula (I) as long as it does not significantly affect in a negative way the compound's ability to link to the target receptor.

The biomodifier is preferably based on a monodisperse PEG building block comprising 1 to 10 units of said building block, said biomodifier having the function of modifying the pharmacokinetics and blood clearance rates of the said agents. In a preferred embodiment of this invention, the compound of formula IV, represents a biomodifier unit comprised of polymerisation of the monodisperse PEG-like structure, 17-amino-5-oxo-6-aza-3,9,12,15-tetraoxaheptadecanoic acid.

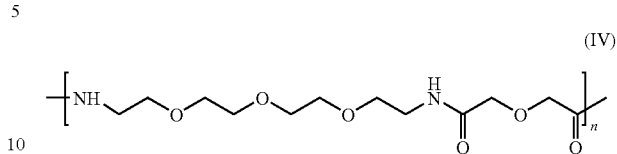

(IV)

wherein n equals an integer from 1 to 10 and where the C-terminal unit forms an amide bond.

Examples of pharmaceuticals of formula (I) are represented by:

Compounds of the formula (II) and (III):

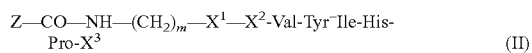

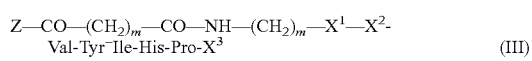

where m is an integer of between 1 and 5 and Z, $X^1$, $X^2$ and $X^3$ are as defined previously.

Compounds defined by formula Va and VIa:

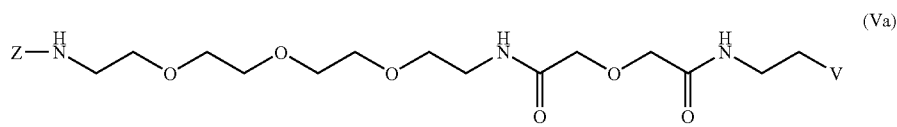

(Va)

(VIa)

where Z and V are as defined previously.

Compounds of the formula (IX):

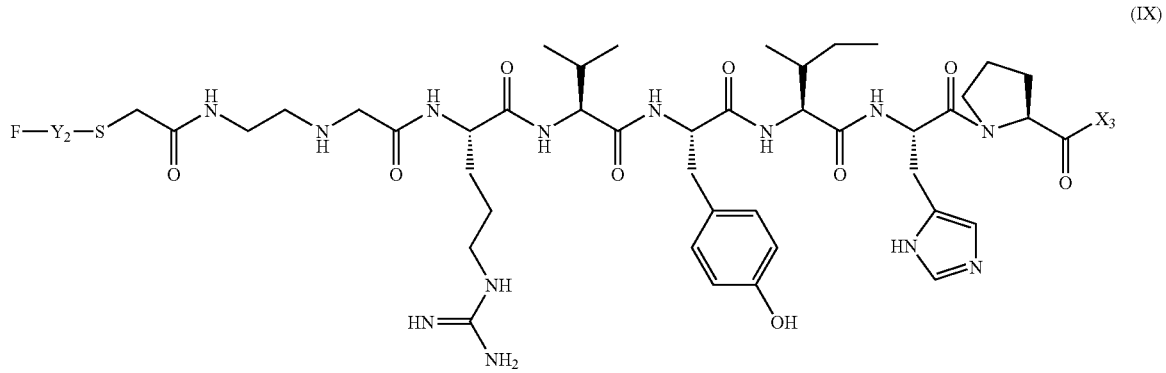

(IX)

where $Y^2$ is alkyl, aryl or a short PEG containing moiety and $Y^2$ is preferably —$CH_2$—$CH_2$—$CH_2$— and $X^3$ is as defined above.

Preferred examples of pharmaceuticals of formula (I) are represented by:

cPN216-Gly-Arg-Val-Tyr-Ile-His-Pro-Ile-OH cPN216-Gly-MeArg-Val-Tyr-Ile-His-Pro-Phe-OH cPN216-Gly-Arg-Val-Tyr-Ile-His-Pro-Ile-OH

N-((CH$_2$)$_6$-tetraamine)-Gly-Arg-Val-Tyr-Ile-His-Pro-Ile-OH

As noted above, for use in in vivo diagnosis the chelates of these compounds with $^{99m}$Tc or $^{18}$F are particularly preferred.

Specifically preferred is the compound cPN216-Gly-Arg-Val-Tyr-Ile-His-Pro-Ile-OH the chemical structure of which is visualised in formula (X):

mammal, such as a human. The administration is suitable carried out by injection or infusion of the formulation such as an aqueous solution. The formulation may contain one or more pharmaceutical acceptable additives and/or excipients e.g. buffers; solubilisers such as cyclodextrins; or surfactants such as Pluronic, Tween or phospholipids. Further, stabilisers or antioxidants such as ascorbic acid, gentisic acid or para-aminobenzoic acid and also bulking agents for lyophilisation such as sodium chloride or mannitol may be added.

In one aspect of the present invention the pharmaceuticals of formula (I) are useful in therapeutic treatment and the monitoring of therapeutic treatment. In the monitoring of the progression of the treatment of heart failure and other diseases where fibrosis is prominent specifically COPD, liver fibrosis and atherosclerosis a method where the subject under treatment is a administered with a pharmaceutical of formula Formula (X)

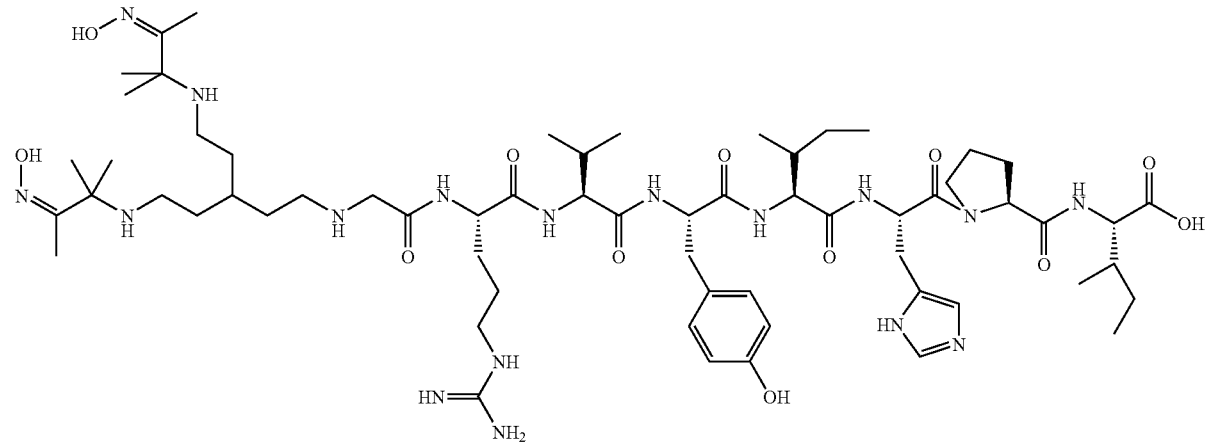

and its chelate with $^{99m}$Tc.

Particularly referred is compound N—((CH$_2$)$_6$-tetraamine)-Gly-Arg-Val-Tyr-Ile-His-Pro-Ile-OH which structure is visualised in formula (XII):

(I) followed by the generation of an image of said subject or parts of said subject.

In a still further aspect a kit for the preparation of a radiopharmaceutical composition of formula (I) comprising a peptide-chelate conjugate and a reducing agent is provided. Preferably the reducing agent of the kit is a stannous salt. The kit may also comprise one or more stabilisers, antioxidants, bulking agents for lyophilisation and solubilisers.

Formula (XII)

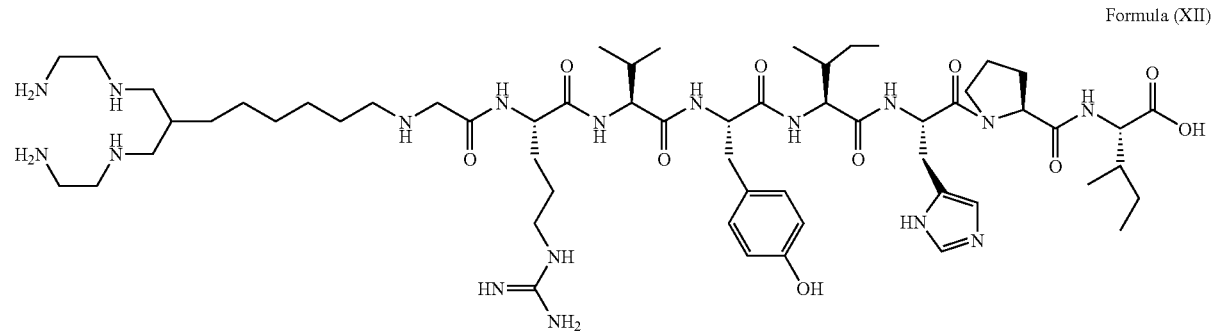

and its chelate with $^{99m}$Tc.

The pharmaceuticals of formula (I) are preferably administered as a pharmaceutical formulation comprising the compound of formula (I) in a form suitable for administration to a General Procedures for the Preparation of the Pharmaceuticals and its Precursors The abbreviations used have the following meanings:

Fmoc: 9-fluorenylmethoxycarbonyl
Boc: t-butyloxycarbonyl
tBu: t-butyl
Trt: trityl
Pmc: 2,2,5,7,8-pentamethylchroman-6-sulfonyl
TFA: trifluoroacetic acid
HBTU: O-Benzotriazol-1-yl-N,N,N',N'-tetramethyluronium hexafluorophosohate
DMF: dimethylformamide
NMP: N-methylpyrrolidone
TIS: triisopropylsilane
NHS: N-hydroxysuccinimidyl
NMM: N-methylmorpholine
RP-HPLC: reversed phase high pressure liquid chromatography
Wang resin: p-benzyloxybenzyl alcohol resin Synthesis of V:

The peptides V of the present invention can be synthesised using all the known methods of chemical synthesis but particularly useful is the solid-phase methodology of Merrifield employing an automated peptide synthesizer (J. Am. Chem. Soc., 85: 2149 (1964)). Typically, the desired sequences are assembled by solid-phase peptide synthesis. Standard procedures for the synthesis strategy employed for the examples of this invention are described in E. Atherton & R. C. Sheppard, "Solid phase peptide synthesis: a practical approach", 1989, IRL Press, Oxford.

For example, a resin with an acid-labile linker group, to which the desired amino-protected C-terminal amino acid residue has been esterified, is used. The amino protecting group is then removed and the second amino acid in the sequence is coupled using a suitable condensation reagent. Amino acids with semi-permanent amino protecting groups and permanent protecting groups for the functional side chains are employed. Amino-deprotection and coupling cycles are then repeated in alternating steps until the sequence of interest is assembled.

Alternatively, the peptides V can be synthesised through solution peptide synthesis methods known in the art, either in a step-wise manner from the carboxyl terminus and/or through the application of segment condensation or ligation methods, employing comprehensive or minimal protection strategies. Combined solution-solid phase segment condensation approaches can also be applied.

Generally, the reactive side-chain groups present (for example amino, hydroxyl, guanidino and carboxyl groups) will be protected during overall synthesis as indicated above. A wide choice of protecting groups for amino acids is known (see, e.g., Greene, T. W. & Wuts, P. G. M. (1991) Protective groups in organic synthesis, John Wiley & Sons, New York). Amino protecting groups which may be employed include 9-fluorenylmethoxycarbonyl (Fmoc) and t-butyloxycarbonyl (Boc). Side-chain protecting groups which may be employed include t-butyl (tBu), trityl (Trt), Boc, and 2,2,5,7,8-pentamethylchroman-6-sulfonyl (Pmc). It will be appreciated that a wide range of other such groups are known in the art.

Finally the permanent side-chain protecting groups are removed and the peptide is cleaved from the resin, usually simultaneously. through treatment with a suitable acidic reagent, e.g. trifluoroacetic acid (TFA).

Conjugation of L to V:

L can be conjugated to V using all the known methods of chemical synthesis. Particularly useful is the nucleophile substitution reaction where a leaving group on the peptide N-terminus is replaced by a nucleophilic group on L. Such a leaving group may be a bromide attached in alpha position to a carbonyl group, and such a nucleophile may be nitrogen.

Conjugation of Z to V or to L:

Z can be conjugated directly to V using the same methods as for the conjugation of L to V. In the case where Z is attached to V via L any methods of chemical synthesis may be used in the conjugation of Z and L. Particularly useful is amide bond formation.

EXAMPLES

Example 1

Ang II Analogues with Dye for Optical Imaging

Fluorescein-NH—$(CH_2)_2$-Gly-Arg-Val-Tyr-Ile-His-Pro-Ile-OH

A peptide analogue of Ang II was synthesised on an Applied Biosystems 433A peptide synthesizer starting with 0.1 mmol Fmoc-Ile-Wang resin. An excess of 1 mmol pre-activated amino acids (using O-Benzotriazol-1-yl-N,N,N',N'-tetramethyluronium hexafluorophosohate (HBTU)) was applied in the coupling steps up to Arg. The N-terminus was bromoacetylated using 0.5 mmol bromoacetic anhydride in DMF for 30 minutes. The bromoacetylated resin was then treated with a solution of 0.5 mmol N-Boc-ethylenediamine dissolved in N-methylpyrrolidone (NMP) for 30 minutes. The simultaneous removal of side-chain protecting groups and cleavage of the peptide from the resins was carried out in 5 mL TFA containing 2.5% triisopropylsilane (TIS) and 2.5% water for two hours. TFA is removed in vacuo, diethyl ether added to the residue and the precipitated peptide washed with diethyl ether and air-dried.

23 mg of crude peptide, 16 mg of fluorescein NHS ester and 12 μL of N-methylmorpholine (NMM) were dissolved in dimethylformamide (DMF) and the reaction mixture stirred over night. Purification of the reaction product by preparative RP-HPLC (Conditions: 5-50% B over 40 min, where A=$H_2O$/0.1% TFA and B=$CH_3CN$/0.1% TFA; flow rate, 10 mL/min; column, Phenomenex Luna 5μ C18 (2) 250×21.20 mm) afforded 19 mg of pure fluorescein-peptide conjugate. The peptide was analysed by analytical HPLC (Conditions: Gradient, 5-50% B over 10 min where A=$H_2O$/0.1% TFA and B=$CH_3CN$/0.1% TFA; flow, 1 mL/min; column, Phenomenex Luna 3μ C18 (2) 50×4.6 mm; detection, UV 214 nm; product retention time 8.91 min). Further product characterisation was carried out using electrospray mass spectrometry ($MH^+$ calculated, 1355.6; $MH^+$ found, 1355.2).

In a similar manner Cy5.5 NHS ester (a dye supplied from Amersham Biosciences) may be used to synthesis the dye-peptide conjugate Cy5.5-NH—$(CH_2)_2$-Gly-Arg-Val-Tyr-Ile-His-Pro-Ile-OH.

Example 2

Aga II Analogue with $^{18}F$ for PET Imaging $^{18}F$—$(CH_2)_3$—S—$CH_2CO$—NH—$(CH_2)_2$-Gly-Arg-Val-Tyr-Ile-His-Pro-Ile-OH A peptide analogue of ATII is synthesised on an Applied Biosystems 433A peptide synthesizer starting with 0.1 mmol Fmoc-Ile-Wang resin. An excess of 1 mmol pre-activated amino acids (using HBTU) is applied in the coupling steps up to Arginine. The N-terminus is bromoacetylated using 0.5 mmol bromoacetic anhydride in DMF for 30 minutes. The bromoacetylated resin is then treated with a solution of 0.5 mmol N-Boc-ethylenediamine dissolved in NMP for 30 minutes.

The simultaneous removal of side-chain protecting groups and cleavage of the peptide from the resin is carried out in 10 mL TFA containing 2.5%. TIS and 2.5% water for two hour. TFA is removed in vacuo, diethyl ether added to the residue and the precipitated peptide washed with diethyl ether and air-dried.

The crude peptide is treated with one equivalent of chloroacetic anhydride dissolved in DMF for 30 min. The chloroacetylated peptide is purified using preparative RP-HPLC. $^{18}$F-propyl thiol is conjugated to the pure chloroacetylated peptide to afford a 18F-labelled peptide for PET imaging.

Example 3

Ang II Analogue for $^{99m}$Tc Labelling chelate-peptide conjugate. The product was analysed by analytical HPLC (Conditions: Gradient, 5-50% B over 10 min where A=H$_2$O/0.1% TFA and B=CH$_3$CN/0.1% TFA; flow, 2 mL/min; column, Phenomenex Luna 3μ C18 (2) 50×4.6 mm; detection, UV 214 nm; product retention time 7.02 min). Further product characterisation was carried out using electrospray mass spectrometry (MH$^+$ calculated, 1280.8; MH$^+$ found, 1280.5).

Example 4

Ang II Analogue for $^{99m}$Tc Labelling cPn216-CO-(CH$_2$)$_3$CO-NH-(CH$_2$)$_2$-Gly-Arg-Val-Tyr-Ile-His-Pro-Ile-OH A peptide analogue. of Ang II was synthesised on an Applied Biosystems 433A peptide synthesizer starting with 0.15 mmol Fmoc-Ile-Wang resin. An excess of 1 mmol pre-activated amino acids (using HBTU) was applied in the coupling steps up to Arginine. The N-terminus was bromoacetylated using 0.75 mmol bromoacetic anhydride in DMF for 30

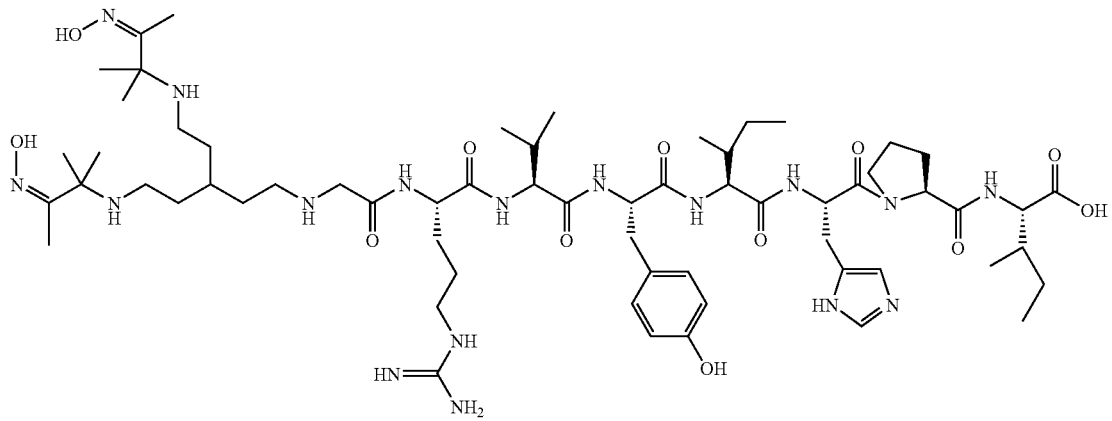

cPn216-Gly-Arg-Val-Tyr-Ile-His-Pro-Ile-OH

A peptide analogue of Ang II was synthesised on an Applied Biosystems 433A peptide synthesizer starting with 0.1 mmol Fmoc-Ile-Wang resin. An excess of 1 mmol pre-activated amino acids (using HBTU) was applied in the coupling steps up to Arginine. The N-terminus was bromoacetylated using 0.5 mmol bromoacetic anhydride in DMF for 30 minutes. The bromoacetylated resin was then treated with a solution of 0.2 mmol cPn216 and 0.4 NMM dissolved in DMF for 16 hours.

The simultaneous removal of side-chain protecting groups and cleavage of the peptide from the resins was carried out in 5 mL TFA containing 5% TIS, 5% water and 2.5% phenol for two hour. TFA is removed in vacuo, diethyl ether added to the residue and the precipitated product washed with diethyl ether and air-dried.

Purification by preparative RP-HPLC (0-30% B over 40 min, where A=H$_2$O/0.1% TFA and B=CH$_3$CN/0.1% TFA, at a flow rate of 10 mL/min on a Phenomenex Luna 5μ C18 (2) 250×21.20 mm column) of the product afforded 12 mg pure minutes. The bromoacetylated. resin is then treated with a solution of 0.75 mmol N-Boc-ethylenediamine dissolved in NMP for 60 minutes.

The simultaneous removal of side-chain protecting groups and cleavage of the peptide from the resins was carried out in 10 mL TFA containing 2.5% TIS and 2.5% water for 90 minutes. TFA is removed in vacuo, diethyl ether added to the residue and the precipitated product washed with diethyl ether and air-dried.

5.5 mg of peptide, 23 mg of cPn216 tetrafluorothiophenyl ester and 10 μL of NMM were dissolved in DMF and the reaction mixture stirred for 3 hrs. Purification by preparative RP-HPLC (conditions: 0-30% B over 40 min, where A=H$_2$O/0.1% TFA and B=CH$_3$CN/0.1% TFA; flow rate, 10 mL/min; column, Phenomenex Luna 5μ C18 (2) 250×21.20 mm) of the product afforded 4.3 mg pure chelate-linker-peptide conjugate. The product was analysed by analytical HPLC (Conditions: Gradient, 5-50 % B over 10 min where A=H$_2$O/0.1% TFA and B=CH$_3$CN/0.1% TFA; flow, 0.3 mL/min; column, Phenomenex Luna 3μ C18 (2) 50×2 mm; detection, UV 214 nm; product retention time 6.51 min). Further product characterisation was carried out using electrospray mass spectrometry ($MH^+$ calculated, 1436.9; $MH^+$ found, 1436.7).

Example 5

Antiarrythmic Effect in a Post Myocardial Infarction (MI) Pig Model

The pharmaceutical cPn216-Gly-Arg-Val-Tyr-Ile-His-Pro-Ile-OH (X) was examined according to the following procedure:

A pig was anaestetised and put on artificial overpressure ventilation. Access to the heart was obtained by a midline sternotomy and removal of the anterior pericardium. The LAD artery was occluded by ligation above the $2^{nd}$ branch and one of the collaterals was occluded as well. This caused development of frequent ventricular extrasystoles, known to proceed into ventricular tachycardia and fibrillation within minutes from previous experiments with the same type of preparation. Complete stabilisation of the condition with return to sinus rhythm occurred within few minutes after intravenous injection of 0,5 mg of the compound of formula (X). An initial rise in mean blood pressure was noticed. Ventricular extrasystoles reappeared gradually after about 15 minutes and a new injection of 0.5 mg of the compound of formula (X) was given. Again the condition stabilised with regular sinus rhythm. During the following hour a stable sinus rhythm and a slightly reduced but adequate constant blood pressure were recorded. The pig was then given a lethal dose of potassium chloride to terminate the experiment. Analysis of ECG recordings before and after the first injection of compound (x) showed shortening of the duration of QRS complexes, indicating that the antiarrythmic effect could be related to an increase in myocardial conduction velocity.

A similar set of observations was made in a second pig experiment.

The compound of formula (X) has thus been shown to act as an anti-arrythmic drug in this preparation.

Example 6

Synthesis of N—$((CH_2)_6$-tetraamine)-Gly-Arg-Val-Tyr-Ile-His-Pro-Ile-OH

The peptide sequence Arg-Val-Tyr-Ile-His-Pro-Ile was synthesised on an Applied Biosystems 433A peptide synthesizer using Fmoc/tBu strategy starting with 0.25 mmol Fmoc-Ile-Wang resin. An excess of 1 mmol pre-activated amino acids, using O-Benzotriazol-1-yl-N,N,N',N'-tetramethyluronium hexafluorophosohate (HBTU), was applied in the coupling steps. The free N-terminus was bromoacetylated using a solution of 1 mmol bromoacetic anhydride in dimethylformamide for 30 minutes. The bromoacetylated resin (0.05 mmol) was then treated with a solution of 0.15 mmol tetra-Boc-tetraamine chelate dissolved in dimethylformamide for 60 min.

The simultaneous removal of side-chain protecting groups and cleavage of the peptide from the resin (0.025 mmol) was carried out in 5 mL trifluoroacetic acid containing 2.5% triisopropylsilane and 2.5% water for 90 min. Trifluoroacetic acid was removed in vacuo, diethyl ether added to the residue and the precipitate washed with diethyl ether and air-dried, affording 25 mg crude product.

Purification by preparative RP-HPLC (0-30% B over 40 min, where A=$H_2O$/0.1% TFA and B=$CH_3CN$/0.1% TFA, at a flow rate of 10 mL/min on a Phenomenex Luna 5μ C18 (2) 250×21.20 mm column) of 25 mg of the crude product afforded 6.5 mg semi-pure product. A second purification step (A=$H_2O$/0.1% HCOOH and B=$CH_3CN$/0.1% HCOOH, elsewhere same conditions as above) of the semi-pure product afforded 3 mg pure product. The product was analysed by analytical HPLC (Conditions: Gradient, 0-30% B over 10 min where A=$H_2O$/0.1% HCOOH and B=$CH_3CN$/0.1% HCOOH; flow, 0.3 mL/min; column, Phenomenex Luna 3μ C18 (2) 50×2 mm; detection, UV 214 nm; product retention time, 5.34 min). Further product characterisation was carried out using electrospray mass spectrometry ($MH^+$ calculated, 1196.8; $MH^+$ found, 1196.7).

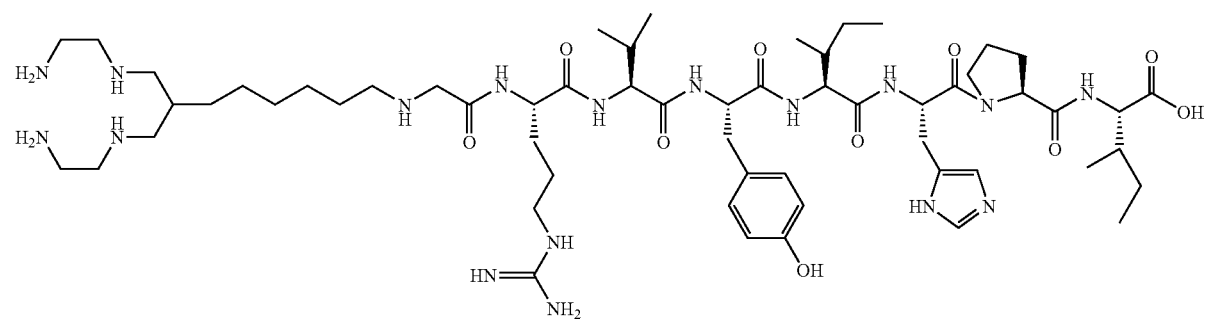

MW = 1196.56
EM = 1195.79
MF = $C_{58}H_{101}N_{17}O_{10}$

Example 7

Synthesis of Hcy3-5; N-cPn216-Gly-Arg-Hcy-Tyr-Hcy-His-Pro-Ile-OH

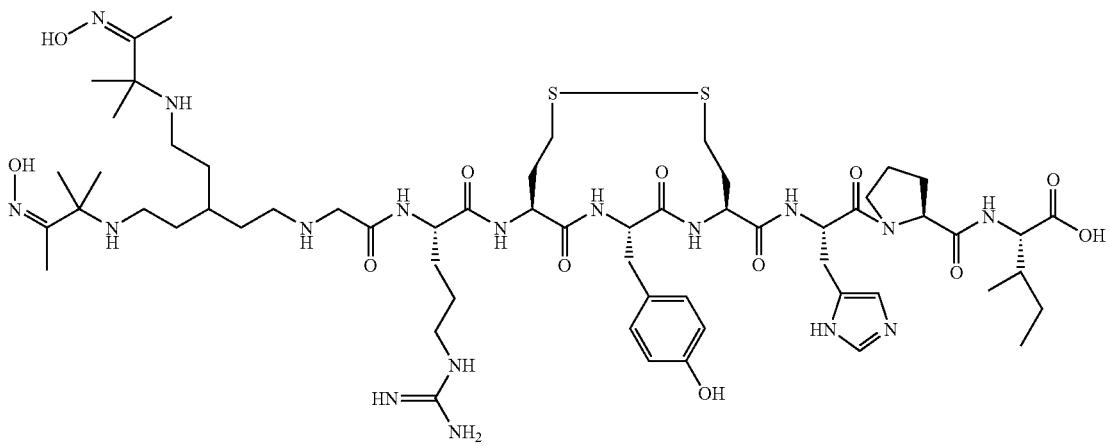

The peptide sequence Arg-Hcy-Tyr-Hcy-His-Pro-Ile was synthesised on an Applied Biosystems 433A peptide synthesizer using Fmoc/tBu strategy starting with 0.25 mmol Fmoc-Ile-Wang resin. An excess of 1 mmol pre-activated amino acids, using O-Benzotriazol-1-yl-N,N,N',N'-tetramethyluronium hexafluorophosohate (HBTU), was applied in the coupling steps. The free N-terminus was bromoacetylated using a solution of 1 mmol bromoacetic anhydride in dimethylformamide for 30 minutes. The bromoacetylated resin (0.05 mmol) was then treated with a solution of 0.25 mmol cPn216 ($^{99m}$Tc-chelate[1]) ([1] for synthesis details see patent WO200300649) dissolved in dimethylformamide for 60 min.

The simultaneous removal of side-chain protecting groups and cleavage of the peptide from the resin was carried out in 10 mL trifluoroacetic acid containing 2.5% triisopropylsilane and 2.5% water for two hour and 20 min. Trifluoroacetic acid was removed in vacuo, diethyl ether added to the residue and the precipitate washed with diethyl ether and air-dried, affording 70 mg crude linear product.

Purification by preparative RP-HPLC (5-50% B over 40 min, where A=H$_2$O/0.1% TFA and B=CH$_3$CN/0.1% TFA, at a flow rate of 10 mL/min on a Phenomenex Luna 5μ C18 (2) 250×21.20 mm column) of the crude linear product afforded 20 mg pure linear product. The linear product was-dissolved in a solution of 2 mL DMSO and 200 mL water and the solution adjusted to pH 8 with ammonia. The solution was stirred for 26 hrs and then adjusted to pH 2 with trifluoroacetic acid.

Purification by preparative RP-HPLC (0-30% B, elsewhere same conditions as above) of the cyclic product afforded 12 mg pure cyclic product. The product was analysed by analytical HPLC (Conditions: Gradient, 5-50% B over 10 min where A=H$_2$O/0.1% TFA and B=CH$_3$CN/0.1% TFA; flow, 0.3 mL/min; column, Phenomenex Luna 3μ C18 (2) 50×2 mm; detection, UV 214 nm; product retention time, 6.01 min). Further product characterisation was carried out using electrospray mass spectrometry (MH$^+$ calculated, 1300.7; MH$^+$ found, 1300.6).

The invention claimed is:

1. A compound of Formula I

(I)

wherein

V denotes a peptide with a binding sequence Gly-$X^2$Val-Tyr-Ile-His-Pro-$X^3$,

L denotes a bond or a linker of formula —NH—$(CH_2)_m$— optionally combined with —CO—$(CH_2)_m$—CO— where m denotes a positive integer from 1 to 10, Z denotes a chelating agent of formula (VII)

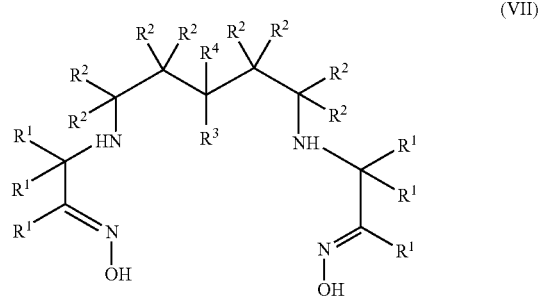

(VII)

wherein:

each $R^1$, $R^2$, $R^3$ and $R^4$ is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring, that optionally can carry an imaging moiety M, $X^2$ denotes Arg, N-alkylated Arg, or Phe[4-guanidino] or Gly-4-piperidyl [N-amidino], $X^3$ denotes an amino acid containing a hydrophobic side-chain, and wherein the residues Val and Ile at position 3 and 5 respectively may optionally be replaced with amino acids capable of forming a bridge containing a —$CH_2$—$CH_2$—, —S—$CH_2$—, —S—$CH_2$—S—, lactam or —S—S— unit, Z forms a bond with the amino acid Gly optionally through the linker L, and M where present denotes a gamma emitting moiety for Radio or SPECT imaging selected from the group of $^{67}$Ga, $^{111}$In, $^{123}$I, $^{125}$I, $^{131}$I, $^{81m}$Kr, $^{99}$Mo, $^{99m}$Tc, $^{201}$Tl and $^{133}$Xe.

2. Compounds of claim 1 having the structures

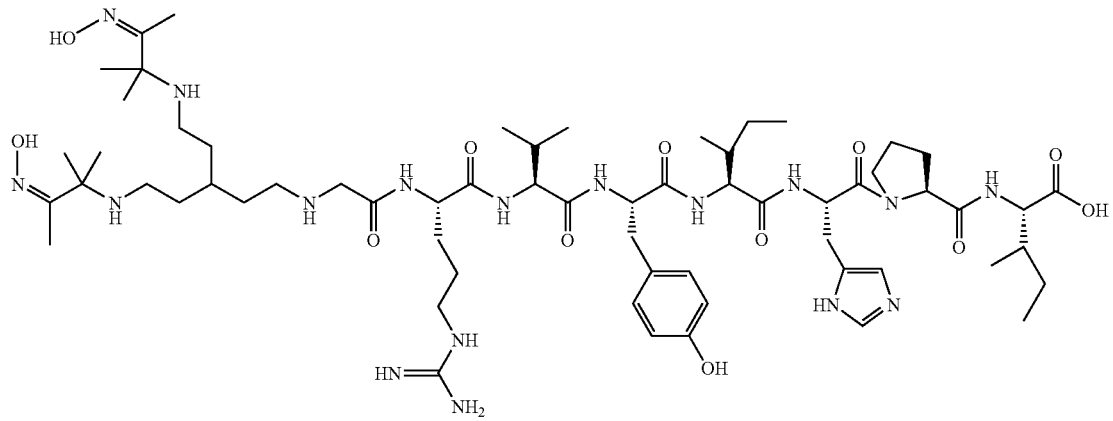

Formula (X)

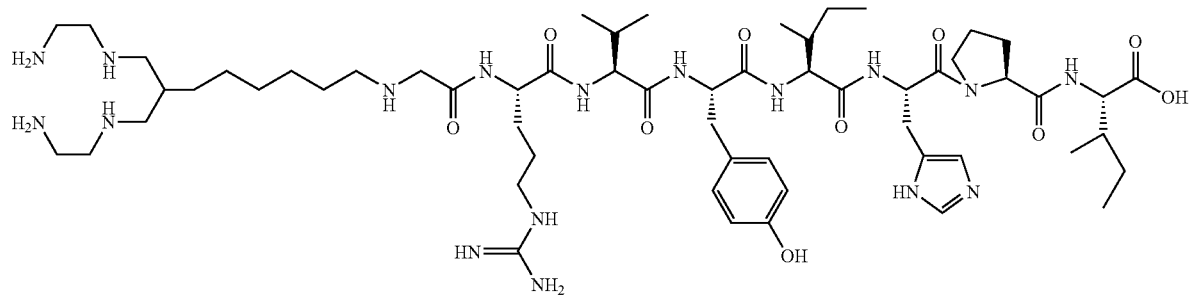

Formula (XII)

-continued

Formula (Xa)

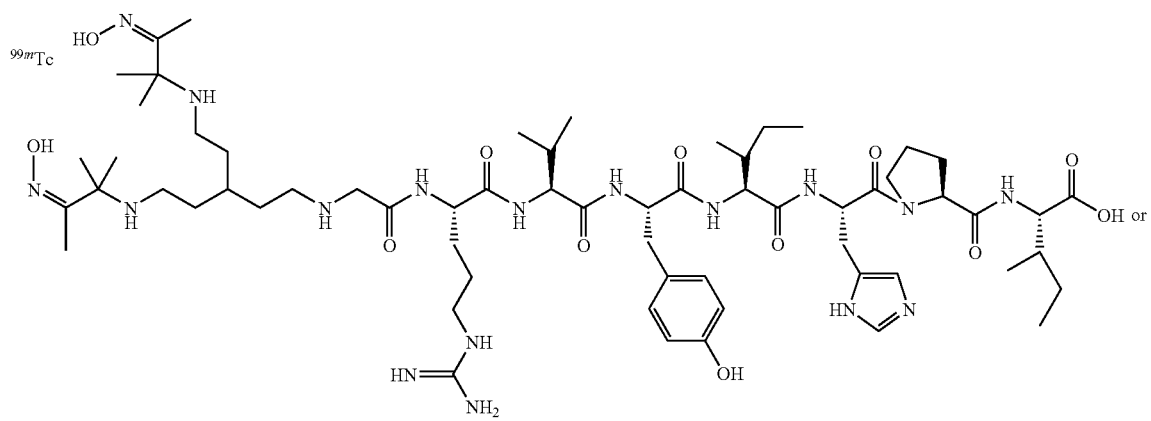

Formula (XIIa)

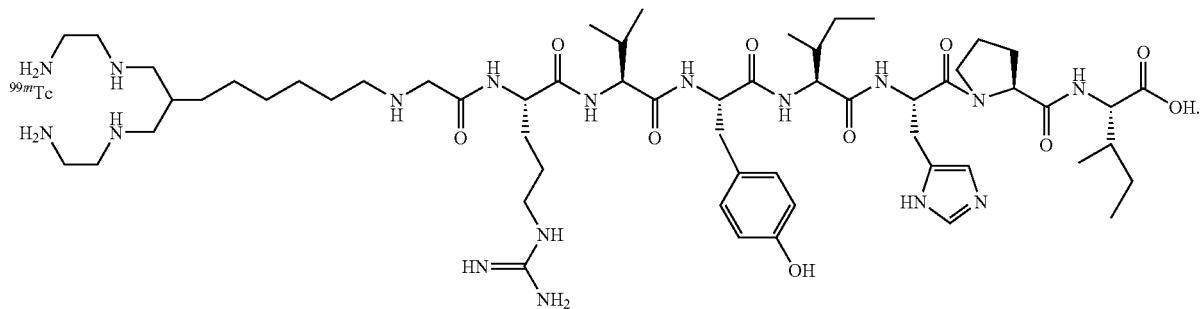

3. A pharmaceutical formulation comprising a compound of formula (I) of claim 1 together with one or more pharmaceutical acceptable additives and/or excipients.

4. A method of treating heart failure, cardiac arrhythmias, COPD (chronic obstructive pulmonary disease), liver fibrosis, and atherosclerosis comprising administering a compound of claim 1 to a person in need thereof.

5. A method of in vivo diagnosis of heart failure, cardiac arrhythmias, COPD (chronic obstructive pulmonary disease), liver fibrosis, and atherosclerosis comprising administering a compound of claim 1 to a subject and generating an image of part or all of said subject.

6. A kit for the preparation of a radiopharmaceutical formulation comprising a compound of claim 1 and a reducing agent.

* * * * *

UNITED STATES PATENT AND TRADEMARK OFFICE
CERTIFICATE OF CORRECTION

PATENT NO. : 7,785,566 B2  Page 1 of 1
APPLICATION NO. : 10/559886
DATED : August 31, 2010
INVENTOR(S) : Alan Cuthbertson, Bard Indrevoll and Morten Eriksen It is certified that error appears in the above-identified patent and that said Letters Patent is hereby corrected as shown below:

Title Page Item 73 should read
Assignee: GE HEALTHCARE AS

Signed and Sealed this

Second Day of November, 2010

David J. Kappos
*Director of the United States Patent and Trademark Office*

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial sequence
<220> FEATURE:
<223> OTHER INFORMATION: Synthesised peptide
<220> FEATURE:
<221> NAME/KEY: misc_feature
<222> LOCATION: (1)..(1)
<223> OTHER INFORMATION: Any amino acid
<220> FEATURE:
<221> NAME/KEY: misc_feature
<222> LOCATION: (2)..(2)
<223> OTHER INFORMATION: Arg, N-alkylated Arg or a mimetic of Arg
<220> FEATURE:
<221> NAME/KEY: misc_feature
```

```
<222> LOCATION: (8)..(8)
<223> OTHER INFORMATION: Amino acid containing a hydrophobic side chain

<400> SEQUENCE: 1

Xaa Xaa Val Tyr Ile His Pro Xaa
1               5

<210> SEQ ID NO 2
<211> LENGTH: 8
<212> TYPE: PRT
<213> ORGANISM: Artificial sequence
<220> FEATURE:
<223> OTHER INFORMATION: Synthesised angiotensin II

<400> SEQUENCE: 2

Asp Arg Val Tyr Ile His Pro Phe
1               5

<210> SEQ ID NO 3
<211> LENGTH: 8
<212> TYPE: PRT
<213> ORGANISM: Artificial sequence
<220> FEATURE:
<223> OTHER INFORMATION: Synthesised peptide

<400> SEQUENCE: 3

Gly Arg Val Tyr Ile His Pro Ile
1               5

<210> SEQ ID NO 4
<211> LENGTH: 8
<212> TYPE: PRT
<213> ORGANISM: Artificial sequence
<220> FEATURE:
<223> OTHER INFORMATION: Synthesised peptide
<220> FEATURE:
<221> NAME/KEY: MISC_FEATURE
<222> LOCATION: (2)..(2)
<223> OTHER INFORMATION: Methylated Arg
<220> FEATURE:
<221> NAME/KEY: MISC_FEATURE
<222> LOCATION: (8)..(8)
<223> OTHER INFORMATION: D-Phe

<400> SEQUENCE: 4

Gly Xaa Val Tyr Ile His Pro Xaa
1               5

<210> SEQ ID NO 5
<211> LENGTH: 8
<212> TYPE: PRT
<213> ORGANISM: Artificial sequence
<220> FEATURE:
<223> OTHER INFORMATION: Synthesised peptide
<220> FEATURE:
<221> NAME/KEY: MISC_FEATURE
<222> LOCATION: (8)..(8)
<223> OTHER INFORMATION: Bip- 2-amino-3-biphenyl propionic acid

<400> SEQUENCE: 5

Gly Arg Val Tyr Ile His Pro Xaa
1               5
```